United States Patent [19]
Hanna

[11] Patent Number: 5,383,021
[45] Date of Patent: Jan. 17, 1995

[54] OPTICAL PART INSPECTION SYSTEM

[75] Inventor: James L. Hanna, Ann Arbor, Mich.

[73] Assignee: Mectron Engineering Company, Ann Arbor, Mich.

[21] Appl. No.: 49,172

[22] Filed: Apr. 19, 1993

[51] Int. Cl.⁶ .................... G01B 11/04; G01B 11/10
[52] U.S. Cl. ................................ 356/383; 250/560; 356/385
[58] Field of Search ............... 356/381, 394, 383, 384, 356/385, 386, 387, 376; 250/560

[56] References Cited

U.S. PATENT DOCUMENTS

| | | |
|---|---|---|
| 2,812,685 | 11/1957 | Vossberg . |
| 3,724,958 | 4/1973 | Callan . |
| 4,067,652 | 1/1978 | Bohlander . |
| 4,122,525 | 10/1978 | Eaton . |
| 4,260,260 | 4/1981 | Letort et al. . |
| 4,395,119 | 7/1983 | Nakata et al. . |
| 4,476,533 | 10/1984 | Daudt et al. . |
| 4,532,723 | 8/1985 | Kellie et al. . |
| 4,576,482 | 3/1986 | Pryor . |
| 4,676,648 | 6/1987 | Schulz et al. . |
| 4,875,777 | 10/1989 | Harding . |
| 4,880,991 | 11/1989 | Boehnlein et al. . |
| 4,914,307 | 4/1990 | Kanev .................... 356/387 |
| 4,978,223 | 12/1990 | Kutchenriter et al. . |
| 4,991,308 | 2/1991 | Donaldson . |
| 5,164,995 | 11/1992 | Brooks et al. .............. 356/383 |

FOREIGN PATENT DOCUMENTS

3633275 10/1987 Germany ................... 356/385

Primary Examiner—F. L. Evans
Attorney, Agent, or Firm—Harness, Dickey & Pierce

[57] ABSTRACT

A non-contact inspection system capable of evaluating spatial form parameters of a workpiece to provide 100% inspection of parts in production. The system causes parts to be sequentially loaded onto an inclined track where they pass through a test section. The test section includes a length detection array for measuring the length of the workpiece, which includes a source generating a sheet of light oriented in the longitudinal direction of the workpiece. The profile of the parts are evaluated by one or more light sources also creating a sheet of light oriented transversed to the longitudinal axis of the parts. Single channel photodetectors are provided for each of the sources which provides an analog output of the extent to which each sheet of light is occluded by the part. These outputs are analyzed through appropriate signal processing hardware and software to generate length and profile data related to the workpiece geometry.

29 Claims, 5 Drawing Sheets

OPTICAL PART INSPECTION SYSTEM

BACKGROUND AND SUMMARY OF THE INVENTION

This invention relates to a device for inspecting components and particularly to one using an array of light sources and photodetectors as a means of evaluating a component for conformance to spatial form criteria.

In this era of emphasis on high quality products, non-contact inspection systems are being used in large numbers. In order for a complex machine to operate as designed all of its sub-components must comply with quality criteria. In some manufacturing settings, 100% inspection of components parts is a requirement of the customer. For example, fasteners used in the automobile industry and elsewhere often must be individually inspected to determine if they meet spatial form and other criteria.

Numerous types of inspection systems are presently used. One general type uses contact probes which touch a component at various points and determines if its dimension or profile meets certain criteria. Contact devices however, have inherent limitations in that they are subject to wear and generally require that the component and the contact probe be accurately positioned during the evaluation process. Moreover, such devices are generally slow to operate and are limited in terms of the number of criteria and complexity of profiles which they can evaluate.

Various non-contact inspection systems are also known using various techniques. For example, ultrasonic inspection systems examine reflected sound waves as a means of characterizing a component. Various systems based on a video image of a part are also known. In addition, laser gauging systems are used in which specific dimensional measurements can be obtained.

In general, however, although known non-contact inspection systems are extremely useful, they have certain limitations. Many of the available non-contact gauging systems require complex data processing approaches which impose expensive hardware requirements and can limit the speed with which evaluations can be accomplished. Preferably, evaluation of a workpiece can be conducted in a rapid enough fashion that the parts can be directly sorted into qualified or disqualified part streams. Prior art systems also tend not to be easily adapted to various parts configurations or for evaluating different features of a part. Moreover, many of the currently available non-contact inspection systems have limitations in terms of the number of parameters which can be effectively examined during the inspection process. Another disadvantage of some known system is their limitations in terms of the types of parameters which can be considered. For example, often fine details of thread profiles of fasteners are needed. Moreover, many prior art systems, although performing adequately in a laboratory setting, are not sufficiently rugged for a production environment where temperature variations, dust, dirt, cutting fluids, etc. are encountered.

In accordance with this invention, a non-contact inspection system is provided which enables rapid inspection to be conducted permitting parts to be immediately sorted in terms of being in conformance or out of conformance with spatial form criteria. Moreover, a hard copy of part geometry can be generated pointing out specific form discrepancies, for example, for a threaded fastener, the diameter, length, profile and threads can be evaluated. In the case of the production of fasteners, the process often begins with wire stock which is fed into a cold heading or screw type forming machine. The part is die-formed or cut in a machine into a shape that may include several diameters and possibly a threaded or knurled length. The formed part may require secondary operations such as thread rolling, heat treating, plating etc. It is not uncommon for one or more of the processes to fail to produce the desired geometry of part. The occurrence of such defects is often not adequately monitored through random part selection or other quality assurance processes which do not provided 100% inspection. The inspection system of this invention is also highly adaptable for evaluating various components.

In the inspection system of the present invention, parts move by gravity or other means along a track through a test section. Initially, the part length is established through the use of a length detection array having a number of light sources and associated photodetectors. One of the sources generates a sheet of light oriented in the direction of travel of the part. The extent to which the sheet of light is blocked by the part is related to its length. In addition, the part passes through a profile detection array having one or more of light sources whose output is also in the configuration of a sheet of laser light oriented perpendicular to the part motion which cuts through the part as it moves past. Significantly, the evaluation of component length and profile in accordance with this invention is achieved through the use of single channel photodetectors. The use of single channel output photodetectors in accordance with this invention inherently provides advantages in terms of signal processing and data reduction.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
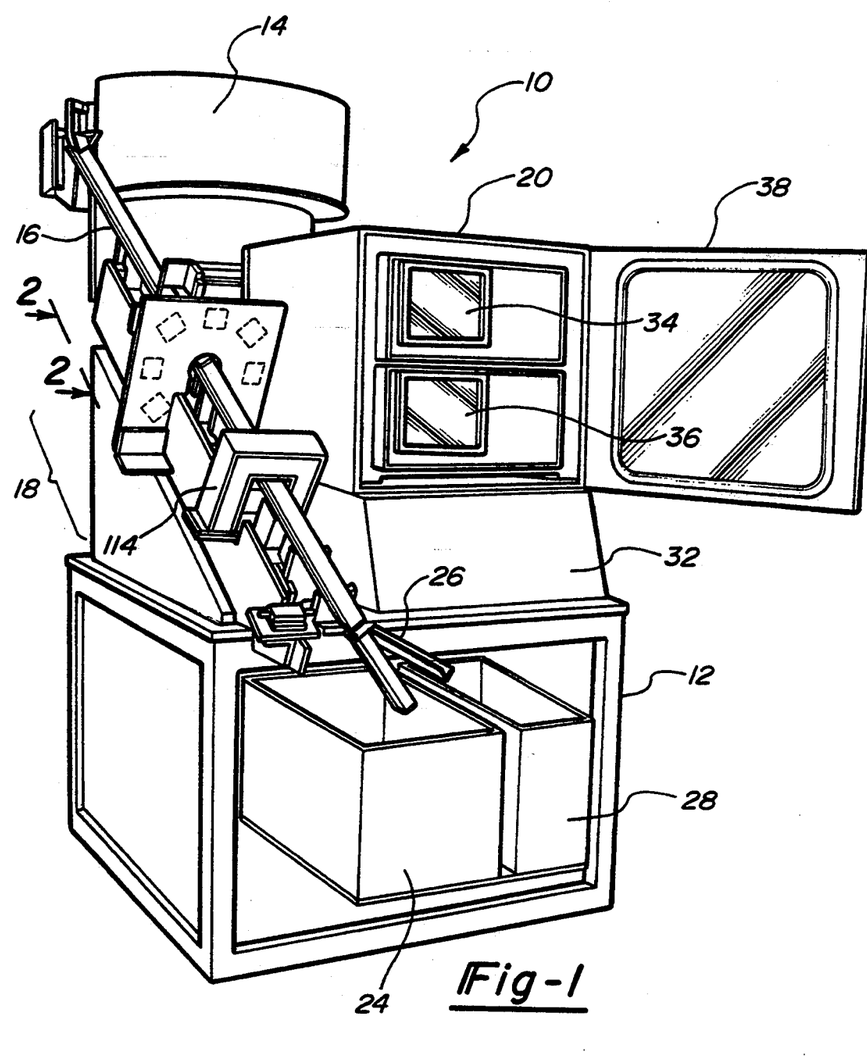
FIG. 1 is a pictorial view of the non-contact inspection system according to this invention.

A non-contact inspection system in accordance with this invention is shown in FIG. 1 and is generally designated there by reference number 10. Inspection system 10 generally comprises frame 12, part sorter 14, slide track 16 having test section 18, and enclosure 20 for housing electronic components of the instrument.

Figure 5:
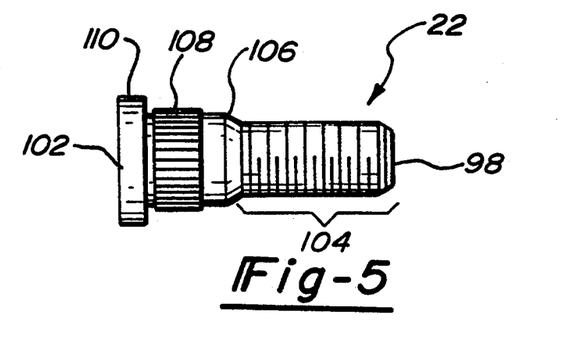
FIG. 5 is an elevational view of a representative workpiece for evaluation.

While inspection system 10 can be used for numerous types of workpieces, an example of one such component is provided in FIG. 5 in the form of a threaded bolt 22 used for mounting the road wheels of a motor vehicle. A large number of bolts 22 (referred to also as "parts" or "workpieces") are dumped into part sorter bin 14. Part sorter 14 causes the randomly oriented bolts 22 to be directed in a desired orientation i.e. headed or threaded end first, and causes them to periodically slide down track 16 under the force of gravity. As parts 22 pass through test section 18, they are evaluated as will be described in more detail in the following portions of this specification. Bolt 22 is inspected for conformance with predetermined spatial form criteria. If a particular part meets the criteria, it passes into parts bin 24 provided for qualified or "good" parts. If, however, the part is deemed to be out of conformance, gate 26 is actuated and the part is diverted into parts bin 28 provided for disqualified or "bad" parts. Presumably, good parts will outnumber bad parts and the parts bins are sized accordingly.

Within enclosure 20 is housed computer 32 provided for evaluating the outputs of the system, controlling the system, and providing a means of storing data related to part criteria and inspection history. A pair of displays 34 and 36 are provided, one of which may output in graphical form configuration data for a particular part, whereas the other may be used for outputting statistical or other numerical data related to inspection. In a prototype embodiment of this invention, displays 34 and 36 were electroluminescent types having touch screens for interaction with the user. Enclosure 20 has access door 38 which can be closed when the system is not in use.

Details of the elements and operation of test section 18 will be described with reference to FIGS. 2 and 3. Within test section 18, two distinct evaluations of part 22 are provided. The length of the part (i.e., its dimension along its direction of travel) is evaluated using length detection array 40, whereas its radial profile (i.e., its form perpendicular to its direction of travel) is evaluated by profile detector array 66.

Length detection array 40 includes length measuring detector 42, and a number of spot laser detectors 44, 46, 48, 50, 52, 54 and 56. Length measuring detector 42 includes a light source 43 which is preferably a semiconductor laser emitting (for convenience) visible light, and photodetector 45. Internally within light source 43 are cylindrical lens elements which spread the beam to define a sheet of light 60 designated by the parallel lines shown in FIG. 2. One laser detector found acceptable for use in conjunction with the present invention is manufactured by the Keyence Company and is designated as model series LX2. Light source 43 provides a sheet of light 60 having a 1 mm thickness (measured perpendicular to the part motion shown by the arrow) and a 30 mm length (measured parallel to the part motion). Since sheet of light 60 is comprised of parallel rays, when a portion of the sheet of light is occluded by part 22, a shadow is created which does not appreciably vary in dimension with distance from the part. Photodetector 45 includes an internal focusing lens and an internal photodiode. As shown in FIG. 2, light source 43 and photodetector 45 are positioned with slide track 16 therebetween. Part 22 interrupts the transmission of light to photodetector 45. A slide track slit 61 allows light to pass through the track when a part is not passing through test section 18.

In operation of length detector array 40, when no portion of sheet of light 48 is occluded, the entire output of laser source 43 is received by photodetector 45 and an electrical output signal is provided based on the uninterrupted light striking the photodetector. However, when any portion of sheet of light 60 is occluded, a corresponding reduction in electrical output from photodetector 45 results. According, photodetector 45 provides an analog output which is a function of the percent of sheet of light 60 which is blocked and therefore not incident upon the photodetector, which is a measure of the length of the part. Although the thickness of sheet of light 60 is not critical, it is narrower than part 22 so that the sheet of light will be occluded as it passes through test section 18.

If parts 22 having a length which is less than the length of sheet of light 60 (i.e. 30 mm is one example) are to be evaluated, no further detectors would be necessary for measuring the length of workpieces beyond length measuring detector 42. This is the case since when such a part is within the confines of sheet of light 60, the proportion of the light which is not occluded is a length measure. However, a longer part fully occludes sheet of light 60 so that the only information provided is that the part length exceeds the length of the sheet of light. However, inspection system 10 is designed to be used with workpiece lengths which exceed that of the length of sheet of light 60. Accordingly, individual length spot detectors 44 through 56 are provided. Each of these devices includes an internal semi-conductor laser source which creates a concentrated beam which is incident upon a surface of V-shaped slide track 16. Length spot detectors 44 through 56 further integrally include a photodetector. These devices are mounted such that when no workpieces are present along slide track 16, the internal photodetector receives a reflected signal from its associated source. The devices are positioned such that when a part 22 slides pass them, the reflected light is interrupted by scattering or reflection, thus enabling the presence of the workpiece at that spot to be determined through a reduced photodetector output.

Figure 2:
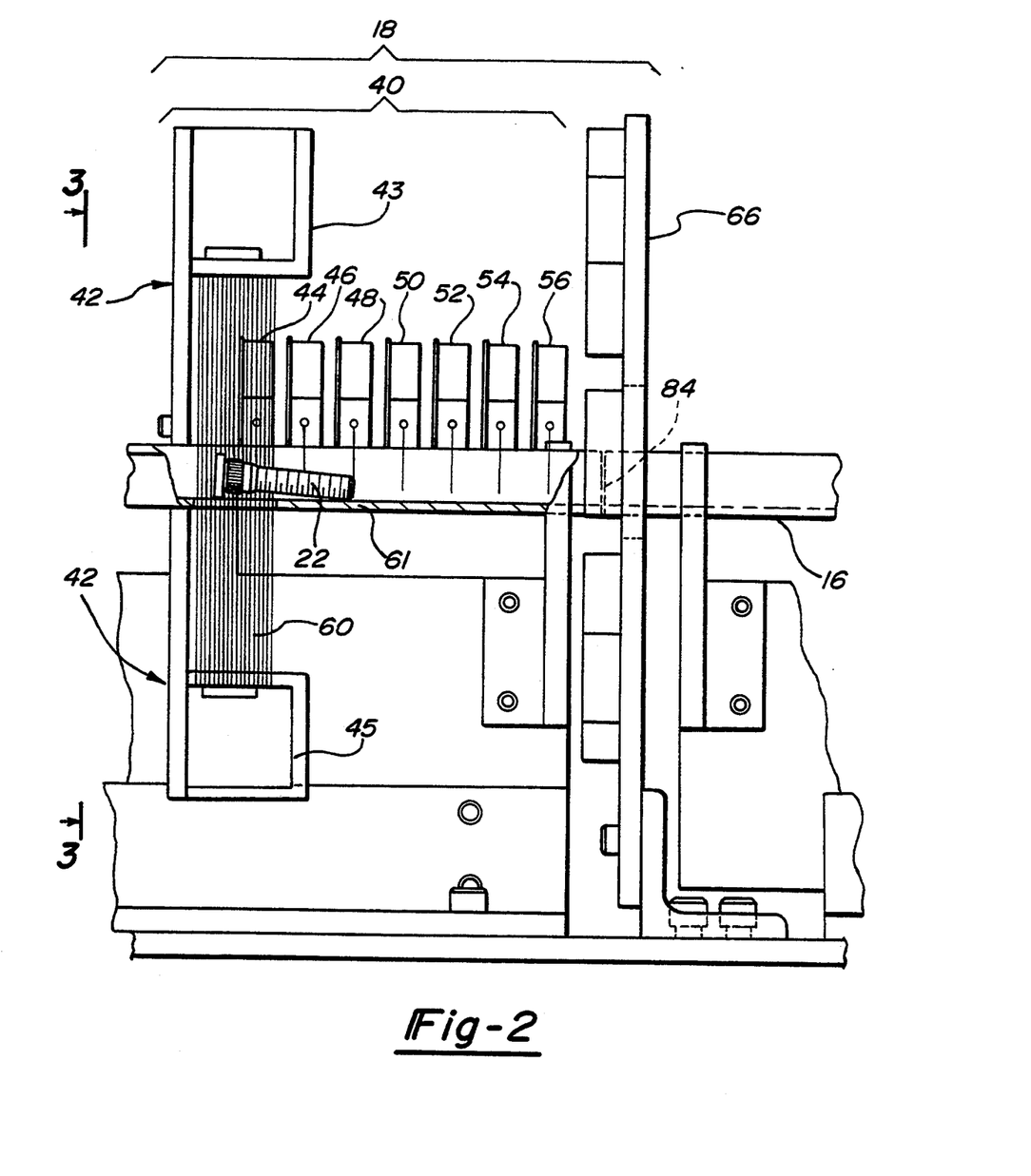
FIG. 2 is a view taken along line 2—2 of FIG. 1 particularly showing the test section and its length detection array.

FIG. 2 shows length spot detectors 44 through 56 located at regular intervals along slide track 16 downstream of length measuring detector 42. Conveniently, length spot detectors 44 through 56 are positioned at one inch intervals or some other regular index location. In operation, when the output of photodetector 45 indicates complete occlusion of sheet of light 60, it is known that the full length of the workpiece 22 cannot be determined solely by the output of photodetector 62. The output of photodetector 62 is evaluated at the instant that each of length spot detectors 44 through 56 first senses the position of the workpiece. In the example shown, this array of spot detectors allows parts having lengths up to 7 inches to be evaluated. As shown in FIG. 2, workpiece 22 is shown at a position as it slides through test section 18 at the threshold of detection by length spot detector 46. Since at this point sheet of light 60 is not completely occluded, it is known that a part length measurement can be made. In this example, the total length of the part is known to be 2 inches added to the length which is measured by the percent of sheet of light 60 being occluded as measured by photodetector 45.

In addition to providing an accurate measure of the length of part 22, length detection array 40 further enables the velocity of the part to be detected if the length of the part is known in advance or can be calculated through evaluation of profile information. As will be described in more detail below, this measure of velocity is important since inspection system 10 does not need the velocity of the part to be accurately controlled through test section 18. Control over workpiece velocity is not needed, allowing use of a simple inclined track by which the parts are directed through test section 18. Moreover, the system's lack of need for accurate velocity control of the part is a distinct advantage since such a requirement would likely add cost and complexity to the system.

Figure 3:
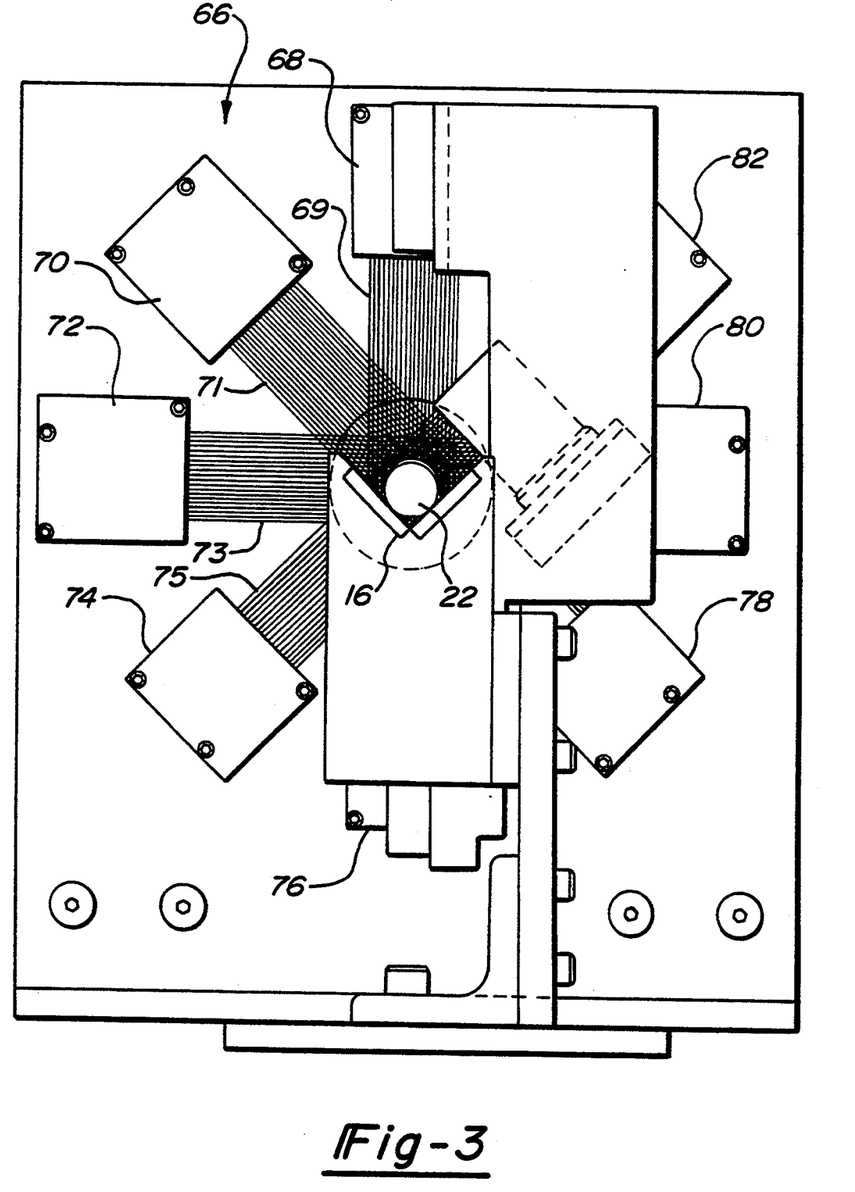
FIG. 3 is a view taken along line 3—3 of FIG. 2 particularly showing the radial detection array of the test section of the instrument in accordance with this invention.

Now with reference to FIG. 3, profile detection array 66 is shown in detail. Profile detection array includes a series of four detectors, having light sources 68, 70, 72 and 74, with corresponding photodetectors 76, 78, 80 and 82, respectively. Each of light sources 68 through 74 are identical to laser light source 43 described previously. Similarly, photodetectors 76 through 80 are identical to photodetector 45 described previously. Accordingly, each of the light sources 68 through 74 generate a sheet of light 69, 71, 73 and 75, respectively, having the characteristics previously described. Like photodetector 45, photodetectors 76 through 82 also integrate the received output of the corresponding light source and provide an analog output related to the percent of occlusion of the associate sheet of light. To permit transmission of the sheets of the light 69 through 75, slide track 16 features a through slit 84 shown in FIG. 2. Sheets of light 69 through 75 are oriented such that the cross-sections of the part are fully within the width of the sheet of light so that the full extent of the cross-section can be evaluated. In the configuration shown, the workpiece 22 has a maximum cross-section thickness which is less than the length of sheets of light 69 through 75. If thicker parts are to be evaluated, additional spot detection could be used as described in connection with the length detector array 40.

If the workpiece 22 is entirely rotationally symmetrical, only a single detector of profile detector array 66 would be needed. However, many workpieces with which inspection system 10 would be used can be expected to have asymmetrical configurations such as flats cut along one portion, threads along their surface, etc. In order to maximize the ability of inspection system 10 to evaluate such various configuration features, four separate laser sources 68 through 74 and associated photodetectors 76 through 82 are provided at 45° angularly displaced positions as shown in FIG. 3.

Figure 4:
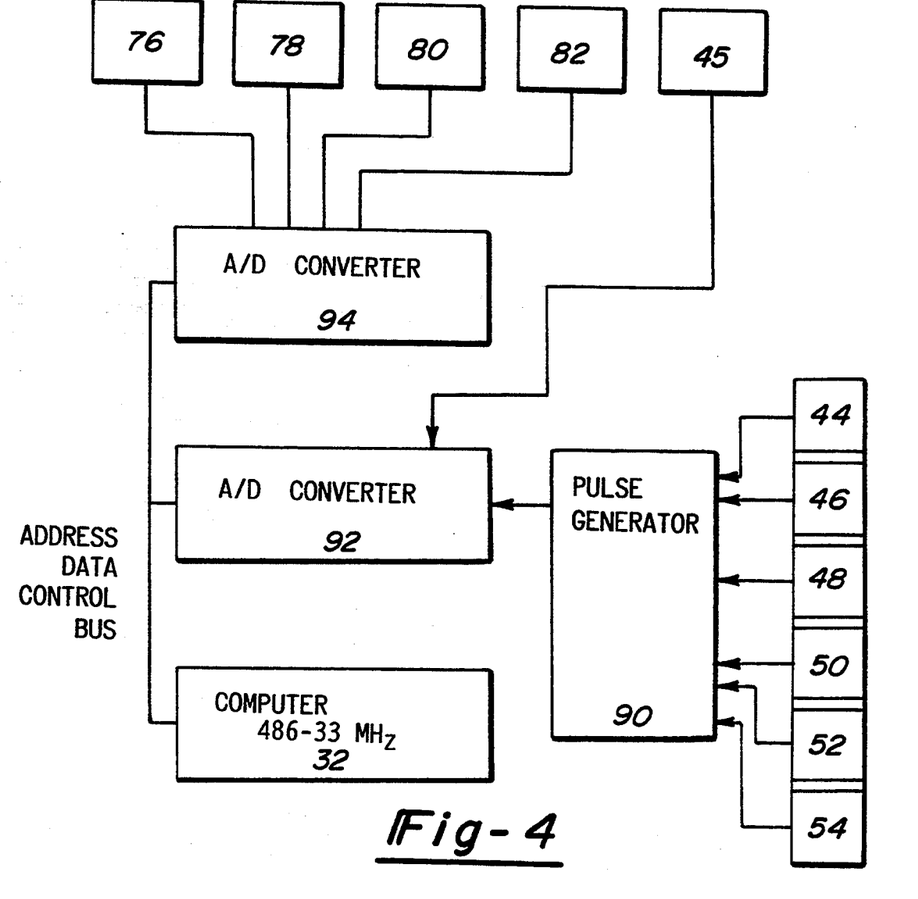
FIG. 4 is a schematic diagram of the photodetectors, light sources and signal processing and control system of the inspection system of this invention.

FIG. 4 provides a schematic diagram of the electronic signal processor and controller 88 of the device of this invention. In an experimental embodiment of the invention an Intel 486 processor based multi-purpose computer 32 is provided to perform many of the functions of processor and controller 88. The length measuring photodetector 45 along with the various spot lasers 44 through 56 fed through pulse generator 90 for shaping their output are fed to analog-to-digital (A to D) converter 92. Converter 92 is externally triggered, for example through the use of a gate or light interrupter which detects parts loaded onto slide rack 16. Profile measuring photodetectors 76 through 82 provide signals fed through A to D converter 94, all of which are processed and displayed through computer 32 and associated displays. A to D convertor 94 is gated under software control based on the output of A to D converter 92.

Figure 6:
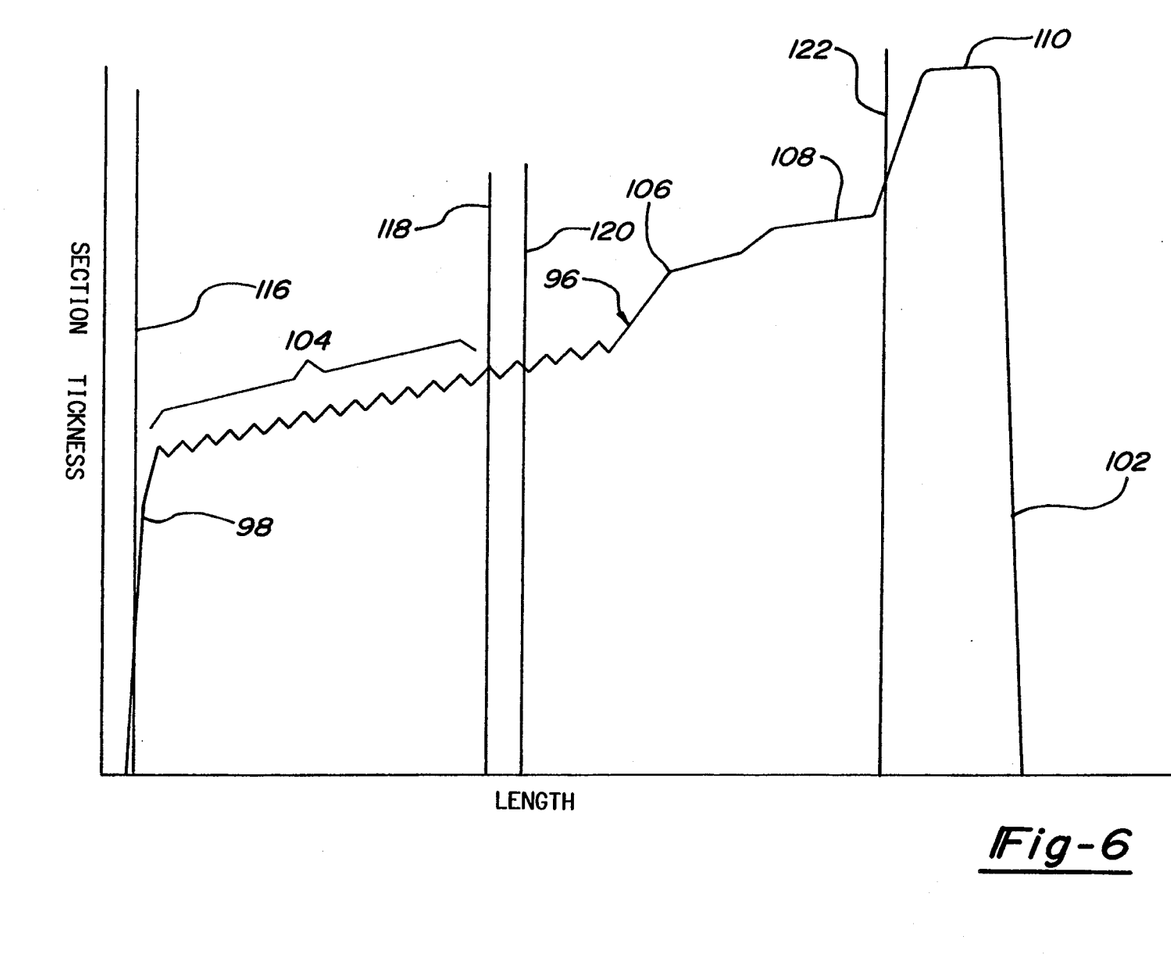
FIG. 6 is a representative output showing a component profile configuration provided by the instrument of the present invention in evaluating the workpiece shown in FIG. 5.

FIG. 6 shows an example profile of the output of laser inspection system 10 generated from inspection of bolt 22 shown in FIG. 5. Although curve 96 resembles a true profile of the part it is instead the analog output of one of photodetectors 76 through 82, plotted with respect to time or length of workpiece 22. In other words, curve 96 is a plot of the section thickness of part 22 along its length. The profile of curve 96, however, clearly designates the ends 98 and 102 of part 22 as well as threaded portion 104, radius 106, knurled section 108, and head 110. Although the velocity of part 22 moving through test section 18 is variable, if its length is known in advance or can be calculated the X axis of curve 96 can be adjusted to display displacement or length as opposed to time which would be velocity sensitive. Since the series of angularly displaced radial measuring detectors generates profiles of the part 22, a plurality of curves similar to 96 are generated simultaneously. Through examining differences in the outputs, the handedness of the threaded portion 104 can be evaluated. In addition, rotationally asymmetric features can be evaluated since it can be assumed that one of the radial detectors 76 through 82 would detect the feature.

Computer 32 provides powerful data evaluation and storage capabilities. Through evaluating a series of parts, various spatial form criteria can be developed. As shown in FIG. 6, various segments of bolt 22 can be created, for example lines 116 and 118 define a threaded portion 104, whereas lines 120 and 122 define a profile section of the bolt. Software can also enable the profile to be displayed in a desired part direction even when the parts are not loaded in one direction only (e.g. head first) compiled data are stored on floppy disc media.

In addition to evaluating various dimensional configuration features of parts 22 inspection system 10 further includes magnetometer 114 which does not form a part of this invention but is shown to demonstrate that other features of work pieces can be evaluated along with spatial form features. Magnetometer 114 enables hardness and internal structural features of the part to be evaluated.

While the above description constitutes the preferred embodiments of the present invention, it will be appreciated that the invention is susceptible of modification, variation and change without departing from the proper scope and fair meaning of the accompanying claims.

I claim:

1. An inspection system for evaluating workpieces for conformance to configuration criteria, comprising:
    track means for causing said workpieces to translate through a test section,
    said test section including a light source for producing a sheet of light having a length greater than its thickness, said light source oriented with respect to said track means such that said workpieces pass through said sheet of light upon passing through said test section, said sheet of light oriented such that said length is parallel to the direction of translation of said workpieces through said test section, said test section further having a photodetector for receiving said sheet of light and providing an output signal related to the intensity of said sheet of light incident on said photodetector, whereby said intensity is related to the degree to which said sheet of light is occluded by said workpieces as said workpieces translate through said test section, and signal processing means for receiving said photodetector output signal and for producing a value related to the length of said workpieces as measured in the direction of said translation.

2. An inspection system according to claim 1 wherein said photodetector provides a single channel output which is an analog signal related to said degree of occlusion.

3. An inspection system according to claim 1 wherein said sheet of light thickness is less than the width of said workpieces measured perpendicular to said direction of translation.

4. An inspection system according to claim 1 wherein said workpieces have a length measured parallel to said direction of translation less than said length of said sheet of light.

5. An inspection system according to claim 1 further comprising at least one light source for generating a point of light and a point photodetector for receiving said point of light within said test section displaced from said sheet of light along said direction of translation whereby the length of said workpieces as measured parallel to said direction of translation can be evaluated by signals from said photodetector and said point photodetector thereby enabling workpieces having a length which exceeds the length of said sheet of light to be evaluated.

6. An inspection system according to claim 1 wherein said signal processing means calculates the velocity of said workpieces moving through said test section.

7. An inspection system according to claim 1 wherein said track means is inclined whereby said workpieces are translated through said test section under the influence of gravity.

8. An inspection system according to claim 1 wherein said sheet of light is comprised of parallel rays whereby said sheet of light length and thickness do not vary appreciably upon passing through said test section.

9. An inspection system according to claim 5 whereby said light source for generating a point of light and said point photodetector are displaced from said sheet of light a distance less than said length of said sheet of light.

10. An inspection system according to claim 7 further comprising a plurality of said light sources for generating a point of light and a corresponding number of point photodetectors with pairs of said light sources and said point photodetectors displaced from said sheet of light a distance less than said length of said sheet of light.

11. An inspection system for evaluating workpieces for conformance to configuration criteria, comprising:
track means for causing said workpieces to translate through a test section,
said test section including a light source for producing a sheet of light having a length greater than its thickness, said light source oriented with respect to said track means such that said workpieces pass through said sheet of light upon passing through said test section, said sheet of light oriented such that said length is perpendicular to the direction of translation of said workpieces through said test section, said test section further having a photodetector for receiving said sheet of light and providing a single channel output signal related to the intensity of said sheet of light incident on said photodetector, whereby said intensity is related to the degree to which said sheet of light is occluded by said workpieces as said workpieces translate through said test section, and
signal processing means for receiving said single channel photodetector output signal and for producing a value related to the section thickness of said workpieces as measured perpendicular to the direction of said translation.

12. An inspection system according to claim 11 wherein said photodetector single channel output is an analog signal related to said degree of occlusion.

13. An inspection system according to claim 11 wherein said sheet of light length is greater than said section thickness.

14. An inspection system according to claim 11 further comprising a plurality of said light sources oriented at angularly displaced positions and having a plurality of said photodetectors associated with said plurality of light sources whereby asymmetry of said workpieces produces different output signals from said plurality of said photodetectors.

15. An inspection system according to claim 11 wherein said track means is inclined whereby said workpieces are translated through said test section under the influence of gravity.

16. An inspection system according to claim 11 wherein said sheet of light is comprised of parallel rays whereby said sheet of light length and thickness do not vary appreciably upon passing through said test section.

17. An inspection system for evaluating workpieces for conformance to configuration criteria, comprising:
track means for causing said workpieces to translate through a test section,
said test section including a first light source for producing a first sheet of light having a length greater than its thickness, said first light source oriented with respect to said track means such that said workpieces pass through first said sheet of light upon passing through said test section, said first sheet of light oriented such that said length is parallel to the direction of translation of said workpieces through said test section, said test section further having a first photodetector for receiving said first sheet of light and providing an output signal related to the intensity of said first sheet of light incident on said first photodetector, whereby said intensity is related to the degree to which said first sheet of light is occluded by said workpieces as said workpieces translate through said test section, said test section including a second light source for producing a second sheet of light having a length greater than its thickness, said second light source oriented with respect to said track means such that said workpieces pass through said second sheet of light upon passing through said test section, said second sheet of light oriented such that said length is perpendicular to the direction of translation of said workpieces through said test section, said test section further having a second photodetector for receiving said second sheet of light and providing an output signal related to the intensity of said second sheet of light incident on said second photodetector, whereby said intensity is related to the degree to which said second sheet of light is occluded by said workpieces as said workpieces translate through said test section, and
signal processing means for receiving said first and second photodetector output signals and for producing values related to the length of said workpieces as measure in the direction of said translation and the cross-sectional configuration of said workpieces as measure perpendicular to said direction of translation.

18. An inspection system according to claim 17 wherein said first photodetector provides a single channel output which is an analog signal related to said degree of occlusion.

19. An inspection system according to claim 17 wherein said second photodetector provides a single channel output which is an analog signal related to said degree of occlusion.

20. An inspection system according to claim 17 wherein said first sheet of light thickness is less than the width of said workpieces measured perpendicular to said direction of translation.

21. An inspection system according to claim 17 wherein said second sheet of light thickness is less than the length of said workpieces measured parallel to said direction of translation.

22. An inspection system according to claim 17 wherein said second sheet of light length is greater than the width of said workpieces measured perpendicular to said direction of translation.

23. An inspection system according to claim 17 further comprising at least one third light source for generating a point of light and a point photodetector for receiving said point of light within said test section displaced from said first sheet of light along said direction of translation whereby the length of said workpieces as measured parallel to said direction of translation can be evaluated by output signals from said point photodetector and said first photodetector thereby enabling workpieces having a length which exceeds the length of said sheet of light to be evaluated.

24. An inspection system according to claim 23 whereby said third light source for generating a point of light and said point photodetectors are displaced from said first sheet of light a distance less than said length of said first sheet of light.

25. An inspection system according to claim 24 further comprising a plurality of said third light sources for generating a point of light and a corresponding number of point photodetectors with pairs of said third light sources and said point photodetectors displaced from said first sheet of light and from each other a distance less than said length of said first sheet of light.

26. An inspection system according to claim 17 wherein said signal processing means calculates the velocity of said workpieces moving through said test section.

27. An inspection system according to claim 17 further comprising a plurality of said second light sources oriented at angularly displaced positions and having a plurality of said second photodetectors associated with said plurality of said second light sources whereby asymmetry of said workpieces produces different output signals from said plurality of said second photodetectors.

28. An inspection system according to claim 17 wherein said track means is inclined whereby said workpieces are translated through said test section under the influence of gravity.

29. An inspection system according to claim 17 wherein said first and second sheets of light are comprised of parallel rays whereby said first and second sheets of light lengths and thicknesses do not vary appreciably upon passing through said test section.

* * * * *